(12) United States Patent
Chang et al.

(10) Patent No.: US 11,950,937 B2
(45) Date of Patent: Apr. 9, 2024

(54) PROBE COVER FOR EAR THERMOMETER AND GROUPING METHOD OF THE SAME

(71) Applicant: RADIANT INNOVATION INC., Hsinchu County (TW)

(72) Inventors: Yung-Chang Chang, Hsinchu County (TW); Tseng-Lung Lin, Hsinchu County (TW); Chin-Hui Ku, Hsinchu County (TW)

(73) Assignee: RADIANT INNOVATION INC., Hsinchu County (TW)

( * ) Notice: Subject to any disclaimer, the term of this patent is extended or adjusted under 35 U.S.C. 154(b) by 484 days.

(21) Appl. No.: 17/225,078

(22) Filed: Apr. 7, 2021

(65) Prior Publication Data
US 2022/0323170 A1     Oct. 13, 2022

(51) Int. Cl.
*A61B 50/00*     (2016.01)
*A61B 5/01*     (2006.01)

(52) U.S. Cl.
CPC ............... *A61B 50/00* (2016.02); *A61B 5/01* (2013.01); *A61B 2050/005* (2016.02); *A61B 2562/247* (2013.01)

(58) Field of Classification Search
CPC ..... A61B 50/00; A61B 5/01; A61B 2050/005; A61B 2562/247
See application file for complete search history.

(56) References Cited

U.S. PATENT DOCUMENTS

2022/0322949 A1 * 10/2022 Chang .................. A61B 5/01
2022/0326083 A1 * 10/2022 Chang .................. G01J 5/0265

FOREIGN PATENT DOCUMENTS

CA       2910295 A1 *  7/2010  ........... A61B 5/0086
WO   WO-2010078219 A1 *  7/2010  ........... A61B 5/0086

* cited by examiner

*Primary Examiner* — Mirellys Jagan
(74) *Attorney, Agent, or Firm* — Li & Cai Intellectual Property Office

(57) ABSTRACT

A probe cover for an ear thermometer and a grouping method of the same are provided. The probe cover for the ear thermometer includes a conical main body having a closed end and an open end, an annular elastomer, and a flange. The closed end is penetrable by infrared rays, and has different infrared transmittances according to thickness variations of the closed end. The annular elastomer is located between the conical main body and the flange. The flange has a plurality of detection positions, each of which having a positive detection pattern or a negative detection pattern, such that the detection positions are arranged to form a plurality of different detection combinations. The different detection combinations respectively correspond to the different infrared transmittances, and any two of the different detection combinations have the two corresponding infrared transmittances that are different from one another.

8 Claims, 13 Drawing Sheets

PROBE COVER FOR EAR THERMOMETER AND GROUPING METHOD OF THE SAME

FIELD OF THE DISCLOSURE

The present disclosure relates to a probe cover for an ear thermometer and a grouping method of the same, and more particularly to a probe cover for an ear thermometer that is placed on a probe of the ear thermometer and a grouping method of the probe cover for the ear thermometer.

BACKGROUND OF THE DISCLOSURE

Conventionally, ear or forehead thermometers are used as body temperature measuring devices to sense a temperature of a human body. However, due to an increased awareness of health and safety, a disposable ear cap is usually placed onto a probe of the ear thermometer before measuring an ear temperature. The ear cap has an infrared transmittance. Generally speaking, a thickness of a top portion the ear cap is relevant to the infrared transmittance of the ear cap. When the ear cap is injection molded, thickness variations of the top portion affect the infrared transmittance, thereby affecting an accuracy of the ear temperature measured by the ear thermometer. To prevent the ear caps from inconsistencies in terms of thickness, manufacturers generally utilize a sifting process to sell the ear caps whose thickness deviations are within a specific range, and throw away those that exceed a tolerance. In the current manufacturing process, there are up to 30% to 40% of the ear caps that need to be thrown away for exceeding the tolerance.

Therefore, by labeling and grouping the ear caps of different thicknesses during the sifting process and by having an improved structural design, how a recognition rate of the infrared transmittance of the ear cap can be increased to overcome the above-mentioned problems has become one of the important issues to be solved in this field.

SUMMARY OF THE DISCLOSURE

In response to the above-referenced technical inadequacies, the present disclosure provides a probe cover for an ear thermometer, and the probe cover includes a conical main body, an annular elastomer, and a flange. The conical main body has a closed end and an open end. The closed end and the open end are arranged opposite to each other, the closed end is penetrable by infrared rays, and the closed end has different infrared transmittances according to thickness variations of the closed end. The annular elastomer is connected to the open end of the conical main body. The flange is connected to the annular elastomer, and the annular elastomer is located between the conical main body and the flange. The flange has a plurality of detection positions. Each of the detection positions has a positive detection pattern or a negative detection pattern, such that the detection positions are arranged to form a plurality of different detection combinations. The different detection combinations respectively correspond to the different infrared transmittances, and any two of the different detection combinations have the two corresponding infrared transmittances that are different from one another.

In another aspect, the present disclosure provides a grouping method of a probe cover for an ear thermometer. The grouping method includes: manufacturing a plurality of probe covers, in which each of the probe covers includes a conical main body, an annular elastomer, and a flange, the conical main body has a closed end and an open end, the closed end and the open end are arranged opposite to each other, and the flange includes at least one recessed portion; using an infrared light beam to penetrate through the closed end of each of the probe covers, so as to obtain an infrared transmittance of the closed end; and grouping the probe covers according to the respective infrared transmittances, and simultaneously processing each of a plurality of detection positions on each of the probe covers of each group. The grouping refers to distinguishing the detection positions on the flange of each of the probe covers. Each of the detection positions has a positive detection pattern or a negative detection pattern, such that the detection positions are arranged to form a plurality of different detection combinations. The different detection combinations respectively correspond to the different infrared transmittances, and any two of the different detection combinations have the two corresponding infrared transmittances that are different from one another.

One of the beneficial effects of the present disclosure is that, in the probe cover for the ear thermometer and the grouping method of the same provided by the present disclosure, through the technical solutions of "the flange of the probe cover having the plurality of detection positions, and each of the detection positions having the positive detection pattern or the negative detection pattern, such that the detection positions are arranged to form the plurality of different detection combinations" and "the different detection combinations respectively corresponding to the different infrared transmittances, and any two of the different detection combinations having the two corresponding infrared transmittances that are different from one another", the ear thermometer that has the probe cover placed thereon can automatically and quickly determine the infrared transmittance of the probe cover, and then calculate and make adjustments according to a value of the infrared transmittance, thereby accurately measuring a temperature of a human body.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
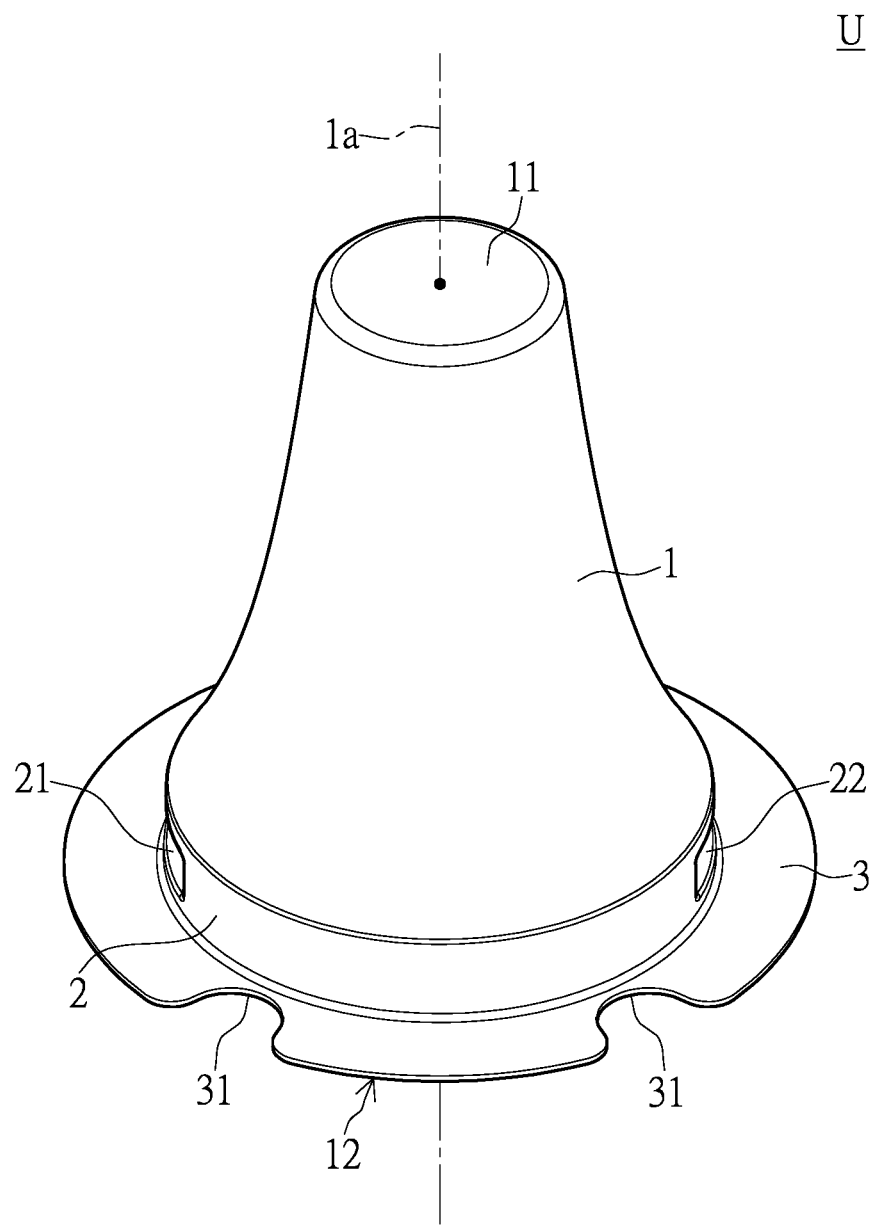
FIG. 1 is a schematic perspective view of a probe cover for an ear thermometer according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
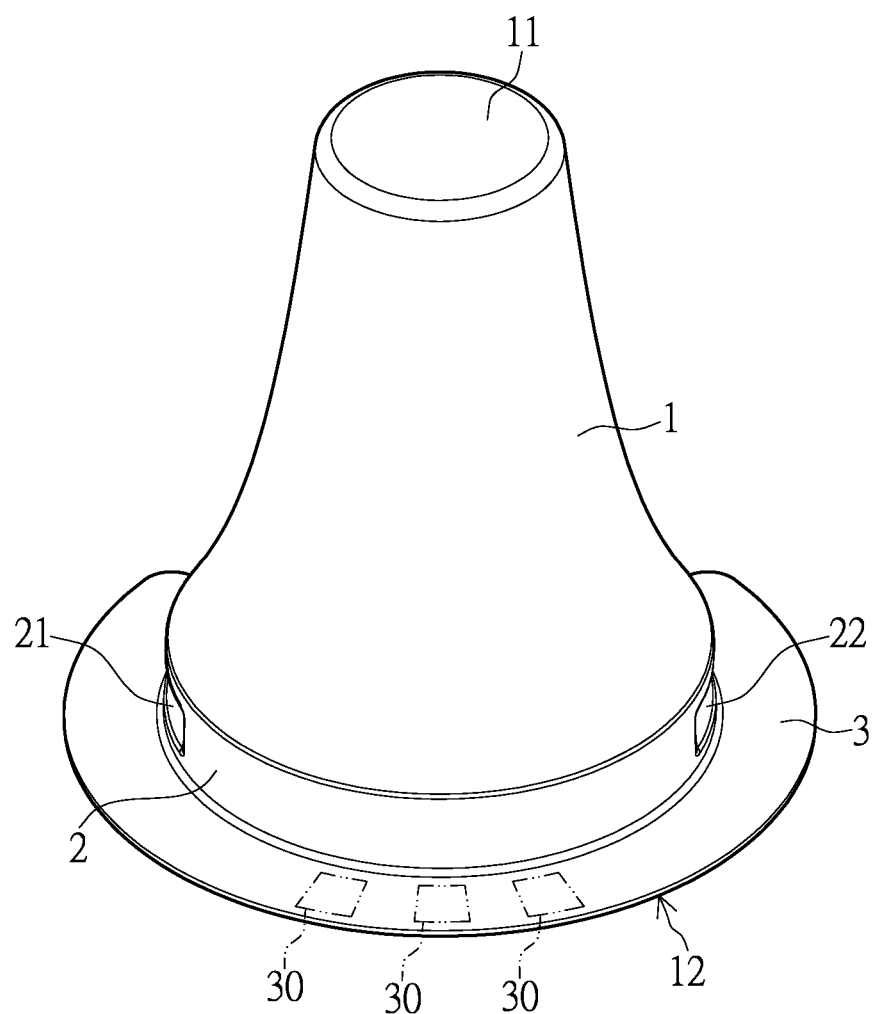
FIG. 2 is another schematic perspective view of the probe cover for the ear thermometer according to the present disclosure.
Figure 3:
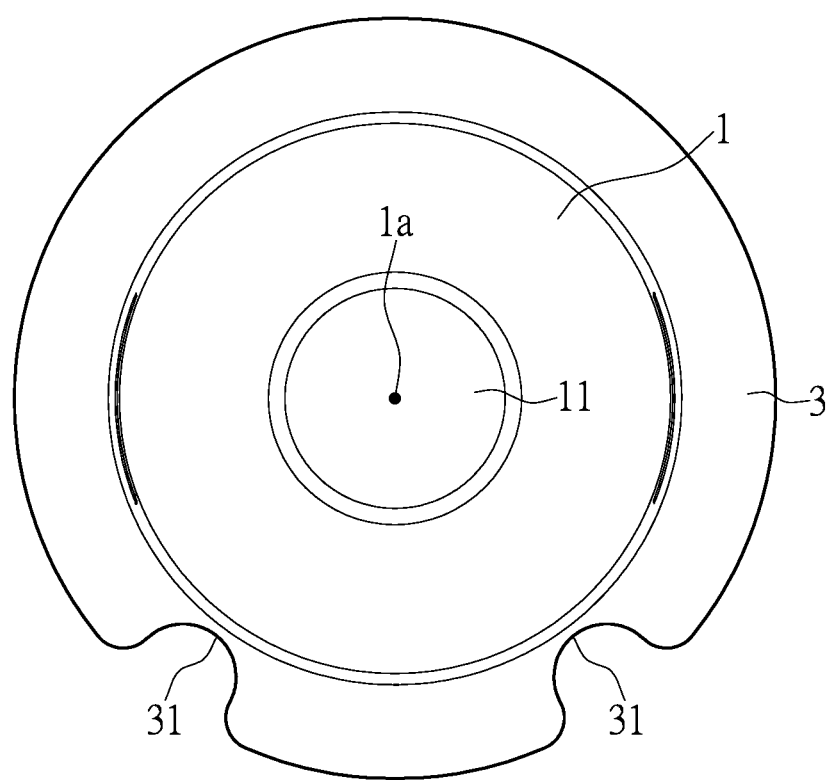
FIG. 3 is a schematic top view of the probe cover for the ear thermometer according to the present disclosure.
Figure 4:
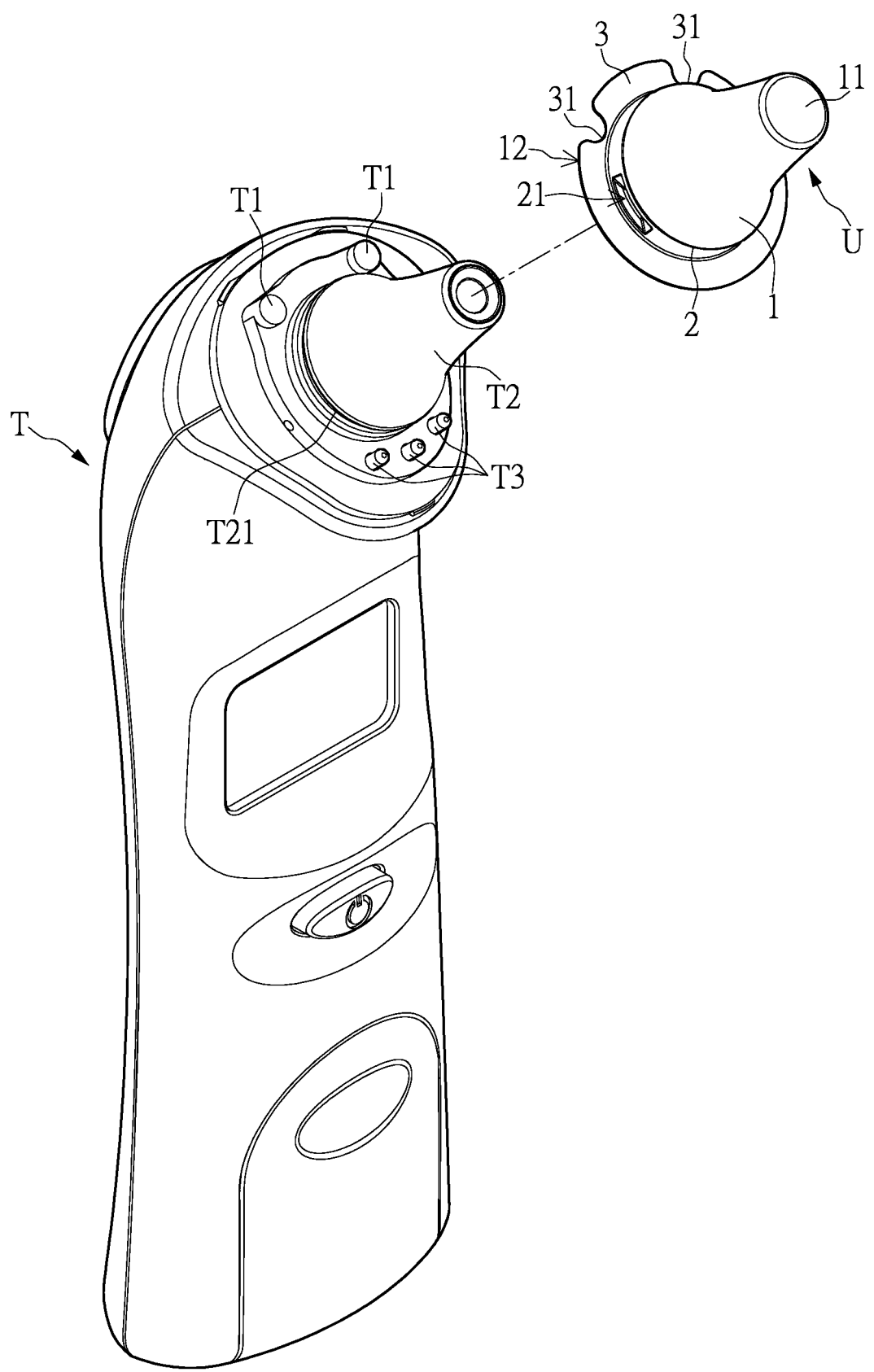
FIG. 4 is a schematic view showing the probe cover for the ear thermometer being placed onto the ear thermometer according to the present disclosure.

Reference is made to FIG. 1 to FIG. 4. FIG. 1 and FIG. 2 are each schematic perspective views of a probe cover for an ear thermometer provided by the present disclosure. FIG. 3 is a schematic top view of the probe cover for the ear thermometer provided by the present disclosure. FIG. 4 is a schematic view showing the probe cover for the ear thermometer being placed onto the ear thermometer according to the present disclosure. A probe cover U for an ear thermometer T is provided by the present disclosure, and the probe cover U is placed onto a probe T2 of the ear thermometer T. In other words, the probe cover U is an ear cap. The probe cover U for the ear thermometer T provided by the present disclosure includes: a conical main body 1, an annular elastomer 2, and a flange 3. The conical main body 1 has a closed end 11 and an open end 12, and the closed end 11 and the open end 12 are arranged opposite to each other. The annular elastomer 2 is connected to the open end 12 of the conical main body 1. The flange 3 is connected to the annular elastomer 2, and the annular elastomer 2 is located between the conical main body 1 and the flange 3. The material of the conical main body 1 can be plastic (for example, but not limited to, polyethylene (PE) or polypropylene (PP)), and has a property of being penetrable by infrared rays, so that the infrared rays can pass through the closed end 11 of the conical main body 1. It should be noted that the infrared rays mentioned herein are mainly infrared rays emitted from a human body. The closed end 11 has a thickness. Since the closed end 11 is penetrable by the infrared rays (i.e., being where the infrared rays mainly pass through), the closed end 11 has different infrared transmittances according to thickness variations thereof. For the probe cover U, an infrared transmittance thereof actually refers to the infrared transmittance of the closed end 11. Therefore, the infrared transmittance of the probe cover U varies according to the thickness variations of the closed end 11. In addition, it should be noted that the probe cover U provided in an embodiment of the present disclosure can be an integrally-formed hard ear cap.

Still referring to FIG. 1 to FIG. 4, the probe cover U further includes at least one recessed portion 31, and the recessed portion 31 is formed on the flange 3. In the present disclosure, a quantity of the recessed portion 31 is two, but is not limited thereto. The conical main body 1 has a central axis 1a, and the central axis 1a passes through a center of the closed end 11 and a center of the open end 12. The recessed portion 31 is recessed in a direction toward the central axis 1a. When the probe cover U is placed on the probe T2 of the ear thermometer T, the recessed portion 31 is engaged with a protrusion T1 of the ear thermometer T. The protrusion T1 is disposed near the probe T2 of the ear thermometer T, and protrudes in a direction parallel to the central axis 1a.

Further, the annular elastomer 2 includes a first abutting portion 21 and a second abutting portion 22 opposite to the first abutting portion 21. The first abutting portion 21 and the second abutting portion 22 are fastened in a groove T21 of the probe T2 of the ear thermometer T, and the groove T21 surrounds an outer surface of the probe T2. Through the first abutting portion 21 and the second abutting portion 22 of the probe cover U being fastened in the groove T21 of the probe T2 of the ear thermometer T, the probe cover U can be stably placed on the probe T2 of the ear thermometer T and does not fall off easily.

Figure 5:
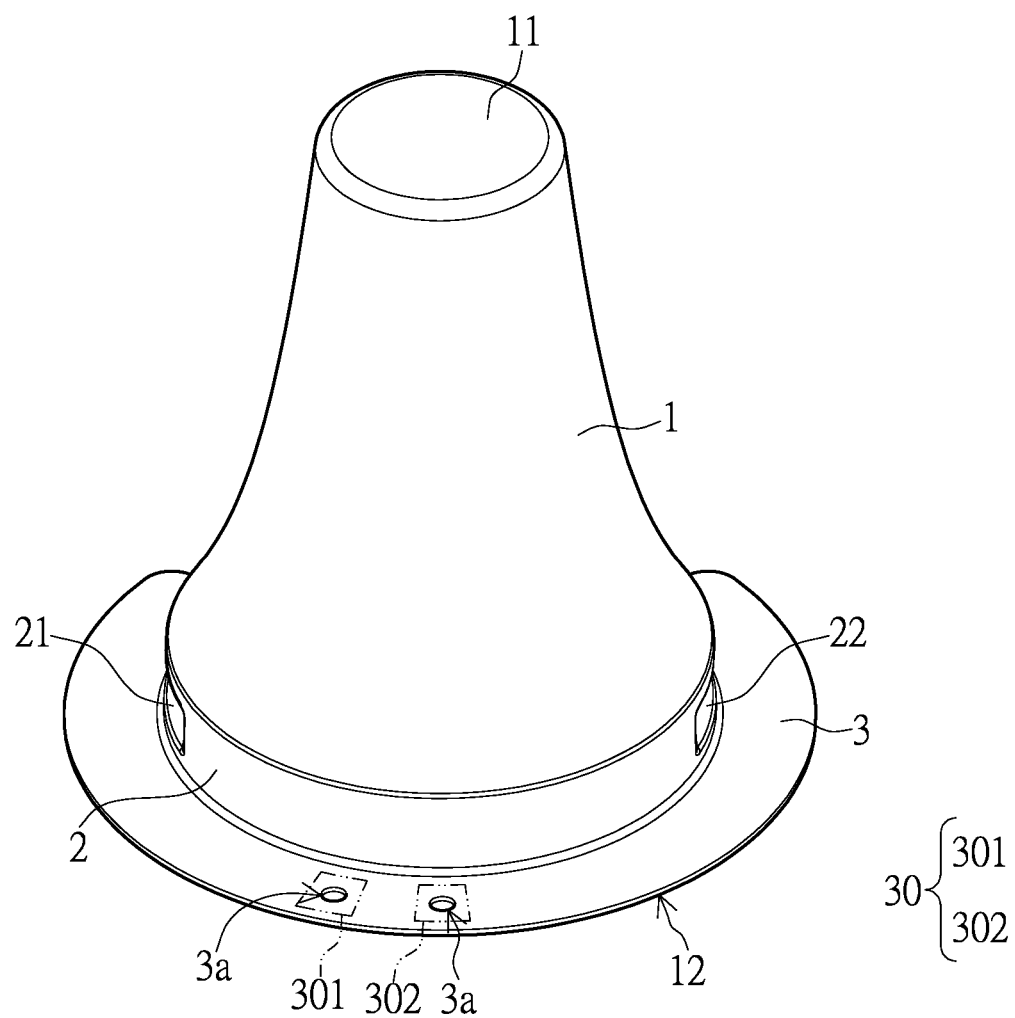
FIG. 5 is a schematic view showing a first detection combination of detection positions of the probe cover for the ear thermometer according to a first embodiment of the present disclosure.
Figure 6:
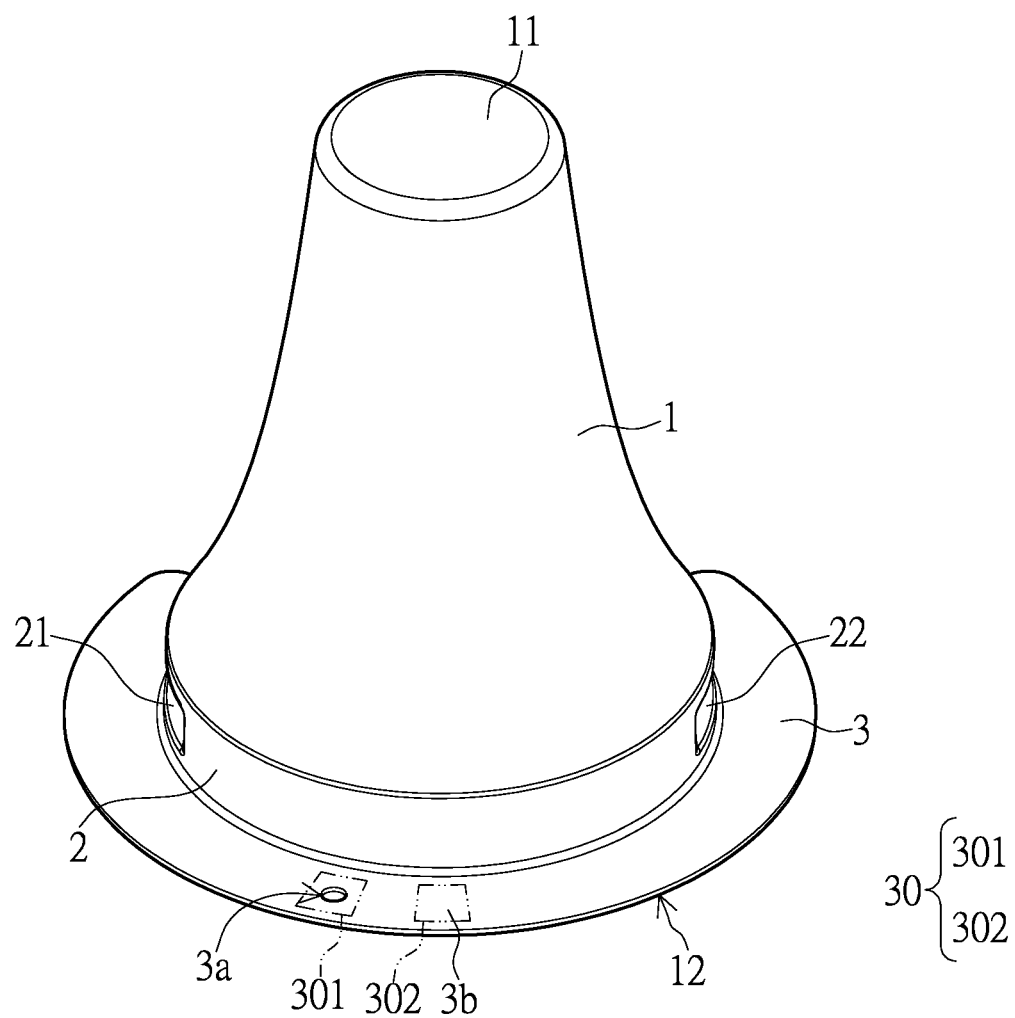
FIG. 6 is a schematic view showing a second detection combination of the detection positions of the probe cover for the ear thermometer according to the first embodiment of the present disclosure.
Figure 7:
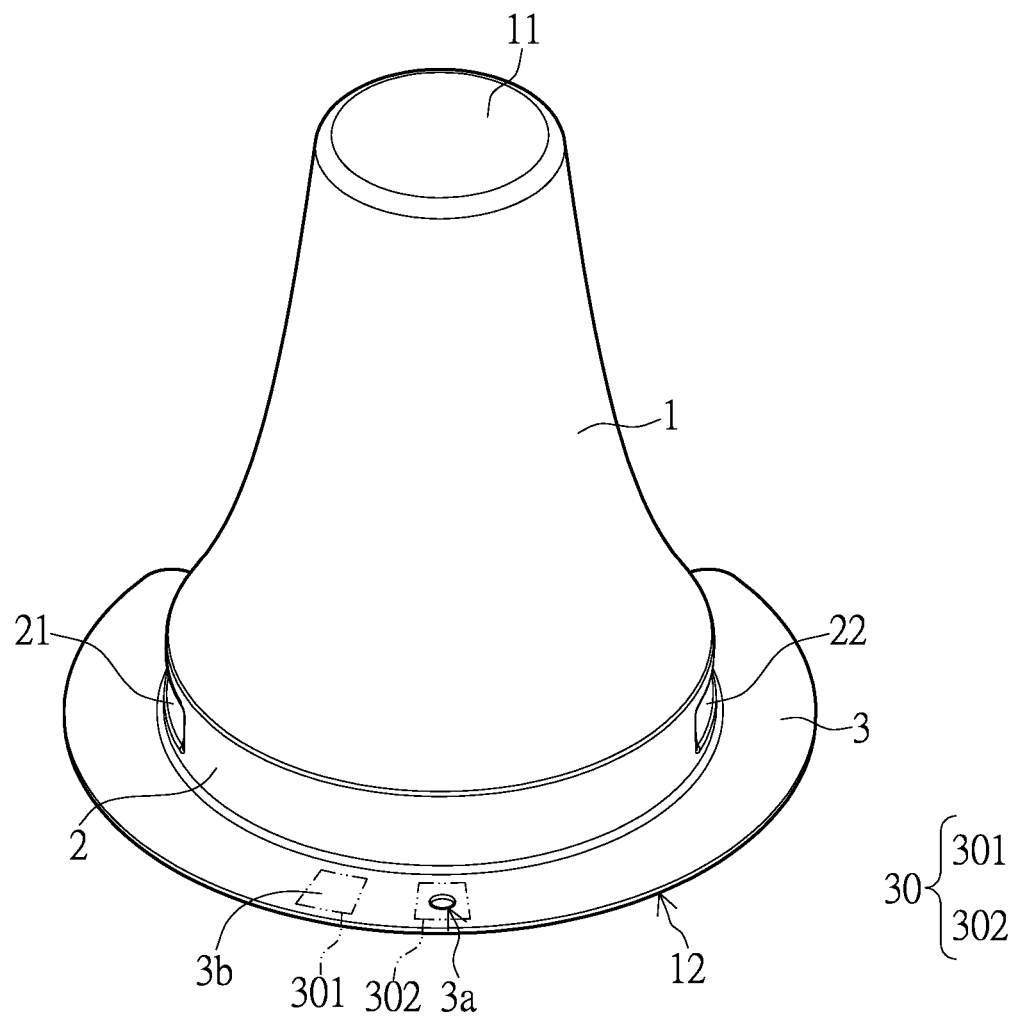
FIG. 7 is a schematic view showing a third detection combination of the detection positions of the probe cover for the ear thermometer according to the first embodiment of the present disclosure.

Next, reference is made to FIG. 5 to FIG. 12. FIG. 5 to FIG. 7 are schematic perspective views showing different configurations of the probe cover for the ear thermometer according to a first embodiment of the present disclosure. FIG. 8 to FIG. 12 are schematic perspective views showing different configurations of the probe cover for the ear thermometer according to a second embodiment of the present disclosure. Specifically speaking, the flange 3 has a plurality of detection positions 30. Each of the detection positions 30 has a positive detection pattern 3a or a negative detection pattern 3b. That is to say, each of the detection positions 30 can be either the positive detection pattern 3a or the negative detection pattern 3b, but cannot be the positive detection pattern 3a and the negative detection pattern 3b at the same time. Each of the detection positions 30 can be one of the positive detection pattern 3a and the negative detection position 3b, such that the detection positions 30 are arranged to form a plurality of different detection combinations. The different detection combinations respectively correspond to the different infrared transmittances, and any two of the different detection combinations have the two corresponding infrared transmittances that are different from one another.

Further, since the probe cover U for the ear thermometer T provided by the present disclosure is placed on the probe T2 of the ear thermometer T, on the ear thermometer T, there are a plurality of activation elements T3 that correspond to the plurality of detection positions 30 on the flange 3 of the probe cover U. When the probe cover U is placed on the probe T2 of the ear thermometer T, the activation elements T3 are in contact with the detection positions 30 on the flange 3 of the probe cover U and activate electronic switches underneath (not shown in the drawings) to emit one or a plurality of signals, thereby detecting the infrared transmittance of the probe cover U. That is to say, through the detection positions 30 on the flange 3 of the probe cover U being arranged to form the plurality of different detection combinations, the activation elements T3 are able to detect an infrared transmittance for each different probe cover U.

Further still, for the probe cover U of the present disclosure, through the engagement of the recessed portion 31 with the protrusion T1 of the ear thermometer T, the detection positions 30 on the flange 3 of the probe cover U can correspond to the activation elements T3 on the ear thermometer T. When the probe cover U is placed on the probe T2 of the ear thermometer T, the design of the recessed portion 31 of the probe cover U can prevent the detection positions 30 from being misaligned with the activation elements T3 due to a rotation of the probe cover U.

It should be noted that in the embodiments described below, the positive detection pattern 3a refers to the flange 3 having an opening formed at the detection positon 30, and the negative detection pattern 3b refers to the flange 3 having no opening formed at the detection position 30. The activation elements T3 of the ear thermometer T that correspond to the detection positions 30 on the flange 3 of the probe cover U can be elastic and pressable mechanical pins that are connected to an electronic switch underneath (not shown in the drawings). However, the present disclosure is not limited thereto. That is to say, in other embodiments of the present disclosure, the positive detection pattern 3a and the negative detection pattern 3b can also be in other forms. For example, the positive detection pattern 3a can refer to the flange 3 being formed by a light-permeable material at the detection position 30, and the negative detection pattern 3b can refer to the flange 3 being formed by an opaque material at the detection position 30 (not shown in the drawings). The activation elements T3 of the ear thermometer T that correspond to the detection positions 30 on the flange 3 of the probe cover U can be optoelectronic switches (optoelectronic sensors). Translucence or opaqueness of the detection positions 30 on the flange 3 of the probe cover U can be used to block a light beam emitted from the optoelectronic switches or allow the same to pass through. In this way, the infrared transmittance of the probe cover U can be detected.

First Embodiment

Reference is made to FIG. 5 to FIG. 7. Specific features of the detection positions 30 on the flange 3 of the probe cover U provided in the first embodiment of the present disclosure will be further illustrated as follows. In the present embodiment, a quantity of the detection positions 30 is set to be two, and a number of the detection combinations is set to be three. The two detection positions 30 are a first detection position 301 and a second detection position 302. The three detection combinations are a first detection combination, a second detection combination, and a third detection combination. It should be noted that, since each of the detection positions 30 has two possibilities (i.e., the positive detection pattern 3a or the negative detection pattern 3b), the two detection positions 30 in the present embodiment can have at most four detection combinations. However, the quantity of the detection combinations actually used can be adjusted according to user requirements, and the present disclosure is not limited to the above-described example.

Reference is made to FIG. 5, which is a schematic view showing the first detection combination of the detection positions of the probe cover for the ear thermometer according to the first embodiment of the present disclosure. The first detection combination refers to the first detection position 301 being the positive detection pattern 3a and the second detection position 302 being the positive detection pattern 3a. In detail, in the first detection combination, the first detection position 301 on the flange 3 of the probe cover U is the positive detection pattern 3a (i.e., an opening is formed at the first detection position 301), and the second detection position 302 on the flange 3 of the probe cover U is also the positive detection pattern 3a (i.e., another opening is formed at the second detection position 302). That is to say, there are two openings formed at the two detection positions 30 on the flange 3 of the probe cover U. Further, an infrared transmittance corresponding to the first detection combination is set to be 80%+/−1%. In other words, when the probe cover U is placed on the probe T2 of the ear thermometer T, the activation elements T3 are in contact with the two detection positions 30 on the flange 3 of the probe cover U, and the infrared transmittance of the probe cover U is detected as 80%+/−1% by a structural feature of the two openings at the two detection positions 30.

Reference is made to FIG. 6, which is a schematic view showing the second detection combination of the detection positions of the probe cover for the ear thermometer according to the first embodiment of the present disclosure. The second detection combination refers to the first detection position 301 being the positive detection pattern 3a and the second detection position 302 being the negative detection pattern 3b. In detail, in the second detection combination, the first detection position 301 on the flange 3 of the probe cover U is the positive detection pattern 3a (i.e., an opening is formed at the first detection position 301), while the second detection position 302 on the flange 3 of the probe cover U is the negative detection pattern 3b (i.e., no opening is formed at the second detection position 302). That is to say, there is only one opening formed at the two detection positions 30 on the flange 3 of the probe cover U. Further, an infrared transmittance corresponding to the second detection combination is set to be 79.5%+/−1%. In other words, when the probe cover U is placed on the probe T2 of the ear thermometer T, the activation elements T3 are in contact with the two detection positions 30 on the flange 3 of the probe cover U, and the infrared transmittance of the probe cover U is detected as 79.5%+/−1% by a structural feature of the opening at the first detection position 301 of the two detection positions 30.

Reference is made to FIG. 7, which is a schematic view showing the third detection combination of the detection positions of the probe cover for the ear thermometer according to the first embodiment of the present disclosure. The third detection combination refers to the first detection position 301 being the negative detection pattern 3b and the second detection position 302 being the positive detection pattern 3a. In detail, in the third detection combination, the first detection position 301 on the flange 3 of the probe cover U is the negative detection pattern 3a (i.e., no opening is formed at the first detection position 301), while the second detection position 302 on the flange 3 of the probe cover U is the positive detection pattern 3a (i.e., an opening is formed at the second detection position 302). That is to say, there is only one opening formed at the two detection positions 30 on the flange 3 of the probe cover U. Further, an infrared transmittance corresponding to the third detection combination is set to be 80.5%+/−1%. In other words, when the probe cover U is placed on the probe T2 of the ear thermometer T, the activation elements T3 are in contact with the two detection positions 30 on the flange 3 of the probe cover U, and the infrared transmittance of the probe cover U is detected as 80.5%+/−1% by a structural feature of the opening at the second detection position 302 of the two detection positions 30.

Moreover, it should be noted that the infrared transmittance of the probe cover U corresponding to each of the above-mentioned detection combinations can actually be configured according to manufacturer requirements, and the present disclosure is not limited thereto. Therefore, in other embodiments, the infrared transmittances of the probe cover U corresponding to the first detection combination, the second detection combination, and the third detection combination do not have to be 80%, 79.5%, and 80.5% (i.e., being the same as the present embodiment), but can be other values (such as 81%, 80%, and 79%).

Second Embodiment

Reference is made to FIG. 8 to FIG. 12. Specific features of the detection positions 30 on the flange 3 of the probe cover U provided in the second embodiment of the present disclosure will be further illustrated as follows. In the present embodiment, a quantity of the detection positions 30 is set to be three, and a quantity of the detection combinations is set to be five. The three detection positions 30 are a first detection position 301, a second detection position 302, and a third detection position 303. The five detection combinations are a first detection combination, a second detection combination, a third detection combination, a fourth detection combination, and a fifth detection combination. It should be noted that, since each of the detection positions 30 has two possibilities (i.e., the positive detection pattern 3a or the negative detection pattern 3b), the three detection positions 30 in the present embodiment can have at most eight detection combinations. However, the quantity of the detection combinations actually used can be adjusted according to user requirements, and the present disclosure is not limited to the above-described example.

Figure 8:
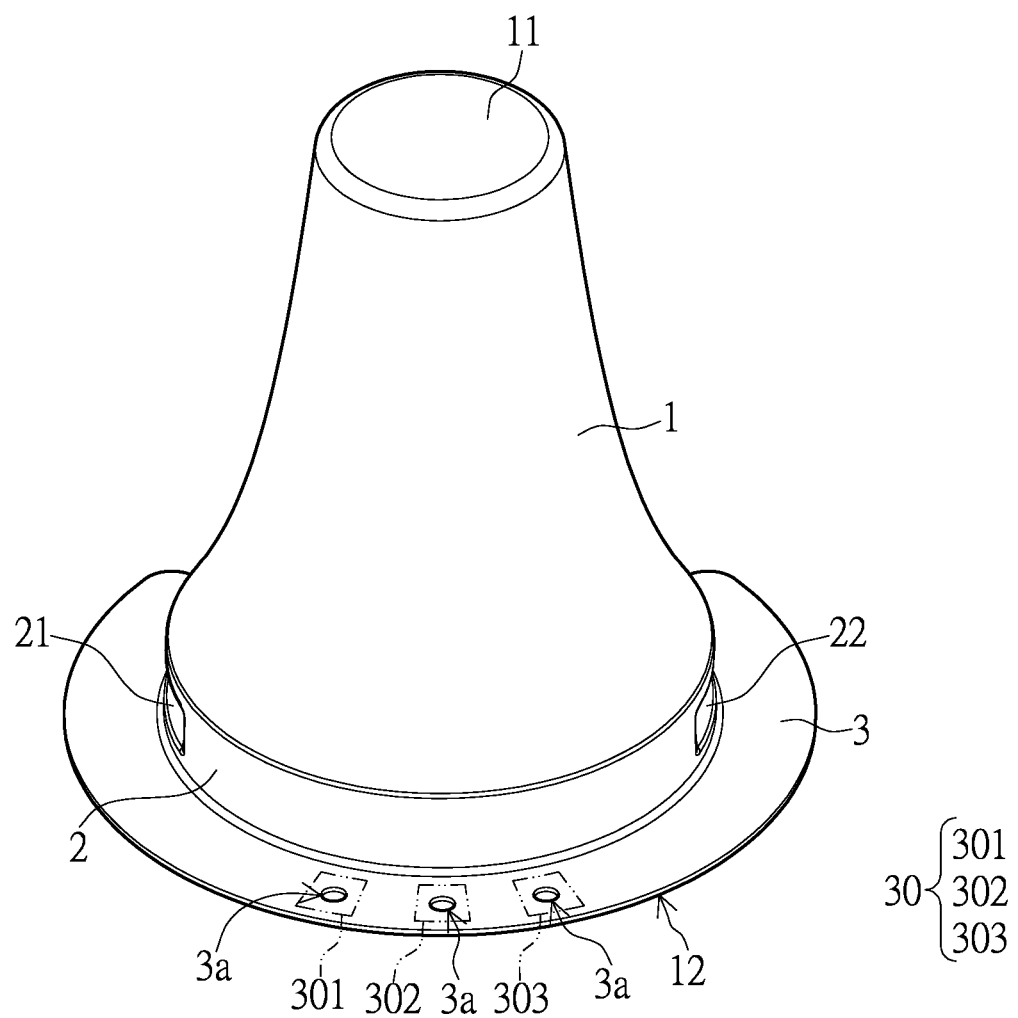
FIG. 8 is a schematic view showing a first detection combination of the detection positions of the probe cover for the ear thermometer according to a second embodiment of the present disclosure.

Reference is made to FIG. 8, which is a schematic view showing the first detection combination of the detection positions of the probe cover for the ear thermometer according to the second embodiment of the present disclosure. The first detection combination refers to the first detection position 301, the second detection position 302, and the third detection position 303 all being the positive detection pattern 3a. In detail, in the first detection combination, the first detection position 301 on the flange 3 of the probe cover U is the positive detection pattern 3a (i.e., an opening is formed at the first detection position 301), the second detection position 302 on the flange 3 of the probe cover U is the positive detection pattern 3a (i.e., another opening is formed at the second detection position 302), and the third detection position 303 on the flange 3 of the probe cover U is the positive detection pattern 3a (i.e., yet another opening is formed at the third detection position 303). That is to say, there are three openings formed at the three detection positions 30 on the flange 3 of the probe cover U. Further, an infrared transmittance corresponding to the first detection combination is set to be 80%+/−1%. In other words, when the probe cover U is placed on the probe T2 of the ear thermometer T, the activation elements T3 are in contact with the three detection positions 30 on the flange 3 of the probe cover U, and the infrared transmittance of the probe cover U is detected as 80%+/−1% by a structural feature of the three openings at the three detection positions 30.

Figure 9:
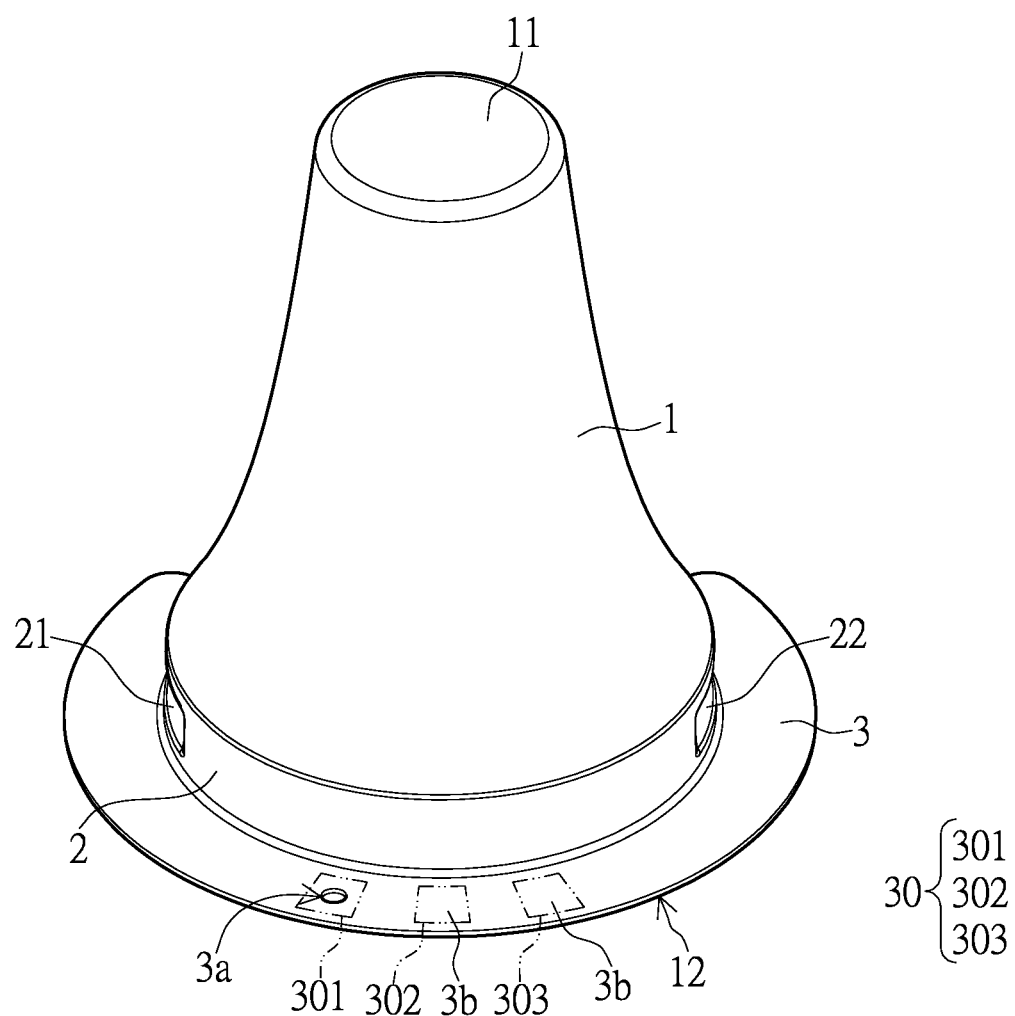
FIG. 9 is a schematic view showing a second detection combination of the detection positions of the probe cover for the ear thermometer according to the second embodiment of the present disclosure.

Reference is made to FIG. 9, which is a schematic view showing the second detection combination of the detection positions of the probe cover for the ear thermometer according to the second embodiment of the present disclosure. The second detection combination refers to the first detection position 301 being the positive detection pattern 3a, the second detection position 302 being the negative detection pattern 3b, and the third detection position 303 being the negative detection pattern 3b. In detail, in the second detection combination, the first detection position 301 on the flange 3 of the probe cover U is the positive detection pattern 3a (i.e., an opening is formed at the first detection position 301), while the second detection position 302 on the flange 3 of the probe cover U is the negative detection pattern 3b (i.e., no opening is formed at the second detection position 302), and the third detection position 303 on the flange 3 of the probe cover U is also the negative detection pattern 3b (i.e., no opening is formed at the third detection position 303). That is to say, there is only one opening formed at the three detection positions 30 on the flange 3 of the probe cover U. Further, an infrared transmittance corresponding to the second detection combination is set to be 80.5%+/−1%. In other words, when the probe cover U is placed on the probe T2 of the ear thermometer T, the activation elements T3 are in contact with the three detection positions 30 on the flange 3 of the probe cover U, and the infrared transmittance of the probe cover U is detected as 80.5%+/−1% by a structural feature of the first detection positon 301 of the three detection positions 30 having the opening.

Figure 10:
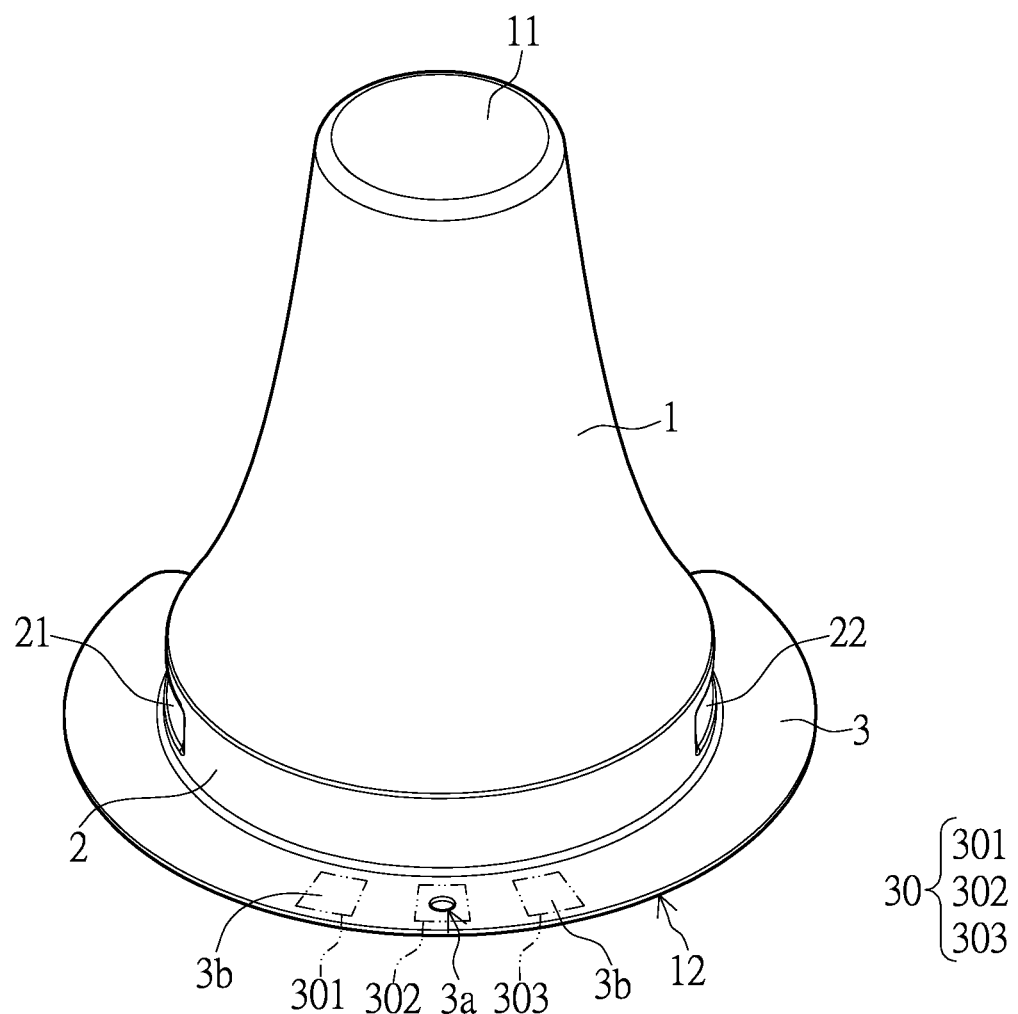
FIG. 10 is a schematic view showing a third detection combination of the detection positions of the probe cover for the ear thermometer according to the second embodiment of the present disclosure.

Reference is made to FIG. 10, which is a schematic view showing the third detection combination of the detection positions of the probe cover for the ear thermometer according to the second embodiment of the present disclosure. The third detection combination refers to the second detection position 302 being the positive detection pattern 3a, and the first detection position 301 and the third detection position 303 being the negative detection pattern 3b. In detail, in the third detection combination, the first detection position 301 on the flange 3 of the probe cover U is the negative detection pattern 3b (i.e., no opening is formed at the first detection position 301), the second detection position 302 on the flange 3 of the probe cover U is the positive detection pattern 3a (i.e., an opening is formed at the second detection position 302), and the third detection position 303 on the flange 3 of the probe cover U is the negative detection pattern 3b (i.e., no opening is formed at the third detection position 303). That is to say, there is only one opening formed at the three detection positions 30 on the flange 3 of the probe cover U. Further, an infrared transmittance corresponding to the third detection combination is set to be 81%+/−1%. In other words, when the probe cover U is placed on the probe T2 of the ear thermometer T, the activation elements T3 are in contact with the three detection positions 30 on the flange 3 of the probe cover U, and the infrared transmittance of the probe cover U is detected as 81%+/−1% by a structural feature of the second detection positon 302 of the three detection positions 30 having the opening.

Figure 11:
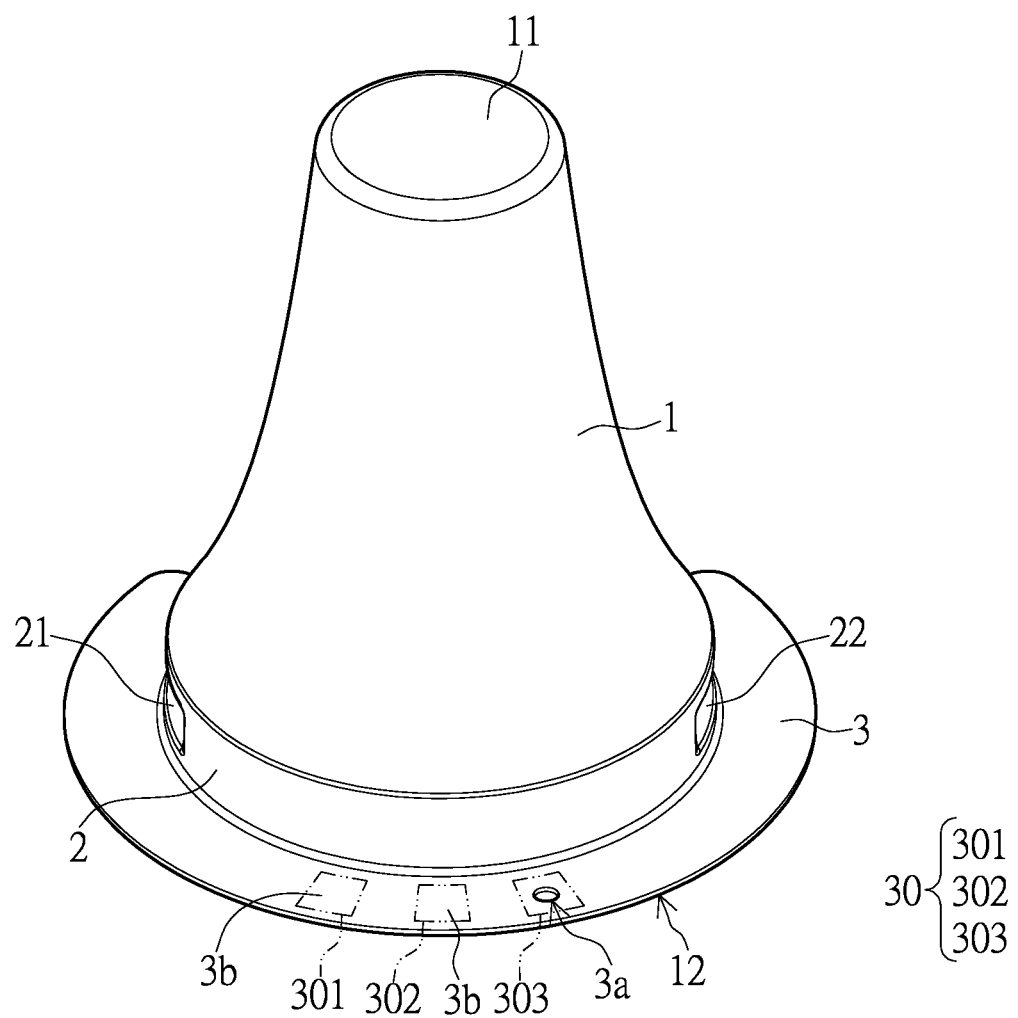
FIG. 11 is a schematic view showing a fourth detection combination of the detection positions of the probe cover for the ear thermometer according to the second embodiment of the present disclosure.

Reference is made to FIG. 11, which is a schematic view showing the fourth detection combination of the detection positions of the probe cover for the ear thermometer according to the second embodiment of the present disclosure. The fourth detection combination refers to the third detection position 303 being the positive detection pattern 3a, and the first detection position 301 and the second detection position 302 being the negative detection pattern 3b. In detail, in the fourth detection combination, the first detection position 301 on the flange 3 of the probe cover U is the negative detection pattern 3b (i.e., no opening is formed at the first detection position 301), and the second detection position 302 on the flange 3 of the probe cover U is also the negative detection pattern 3b (i.e., no opening is formed at the second detection position 302), while the third detection position 303 on the flange 3 of the probe cover U is the positive detection pattern 3a (i.e., an opening is formed at the third detection position 303). That is to say, there is only one opening formed at the three detection positions 30 on the flange 3 of the probe cover U. Further, an infrared transmittance corresponding to the fourth detection combination is set to be 79.5%+/−1%. In other words, when the probe cover U is placed on the probe T2 of the ear thermometer T, the activation elements T3 are in contact with the three detection positions 30 on the flange 3 of the probe cover U, and the infrared transmittance of the probe cover U is detected as 79.5%+/−1% by a structural feature of the third detection positon 303 of the three detection positions 30 having the opening.

Figure 12:
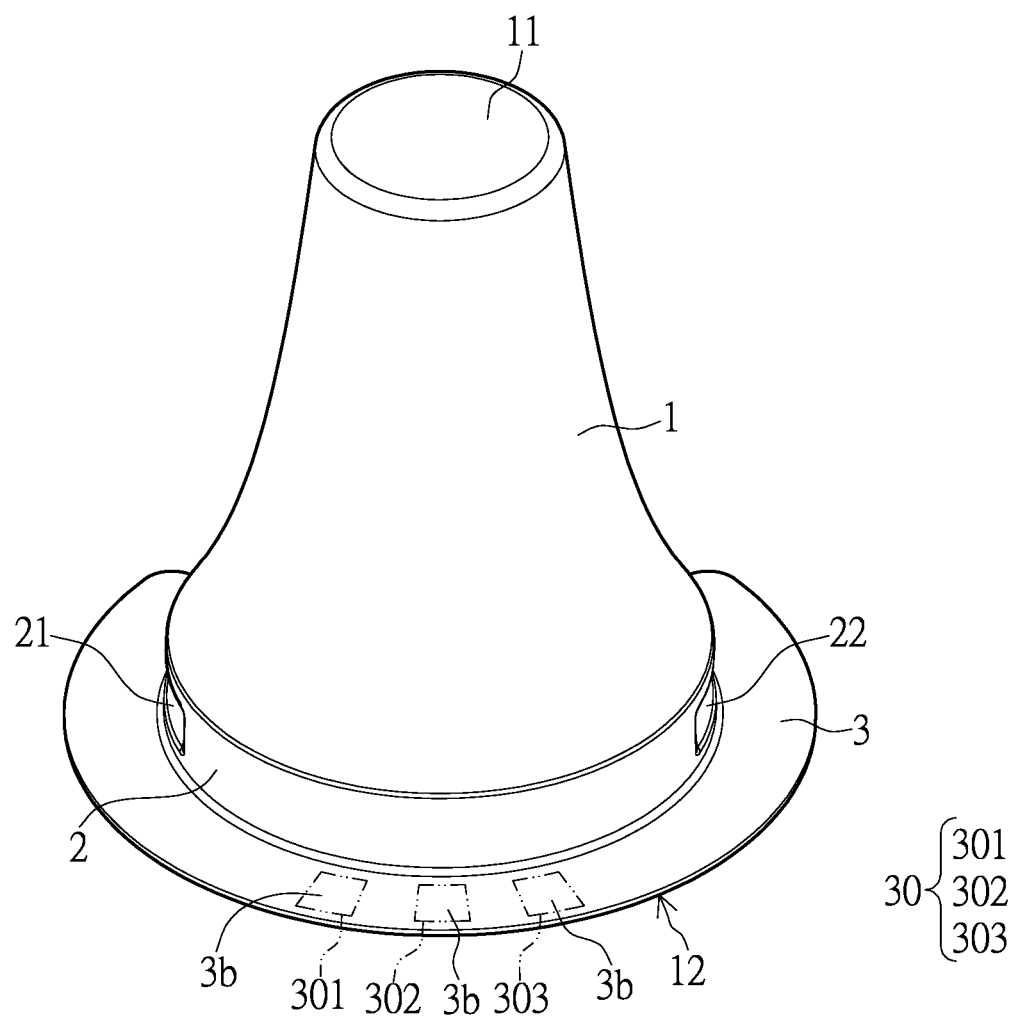
FIG. 12 is a schematic view showing a fifth detection combination of the detection positions of the probe cover for the ear thermometer according to the second embodiment of the present disclosure.

Reference is made to FIG. 12, which is a schematic view showing the fifth detection combination of the detection positions of the probe cover for the ear thermometer according to the second embodiment of the present disclosure. The fifth detection combination refers to the first detection position 301, the second detection position 302, and the third detection position 303 all being the negative detection pattern 3b. In detail, in the fifth detection combination, the first detection position 301 on the flange 3 of the probe cover U is the negative detection pattern 3b (i.e., no opening is formed at the first detection position 301), the second detection position 302 on the flange 3 of the probe cover U is the negative detection pattern 3b (i.e., no opening is formed at the second detection position 302), and the third detection position 303 on the flange 3 of the probe cover U is the negative detection pattern 3b (i.e., no opening is formed at the third detection position 303). That is to say, there is no opening formed at the three detection positions 30 on the flange 3 of the probe cover U. Further, an infrared transmittance corresponding to the fifth detection combination is set to be 79%+/−1%. In other words, when the probe cover U is placed on the probe T2 of the ear thermometer T, the activation elements T3 are in contact with the three detection positions 30 on the flange 3 of the probe cover U, and the infrared transmittance of the probe cover U is detected as 79%+/−1% by a structural feature of the three detection positions 30 not having any opening.

Moreover, it should be noted that the infrared transmittance of the probe cover U corresponding to each of the above-mentioned detection combinations can actually be configured according to user requirements, and the present disclosure is not limited thereto. Therefore, in other embodiments, the infrared transmittances of the probe cover U corresponding to the first detection combination, the second detection combination, the third detection combination, the fourth detection combination, and the fifth detection combination do not have to be 80%, 80.5%, 81%, 79.5%, and 79% (i.e., being the same as those mentioned in the present embodiment), but can be other values, such as 82%, 81%, 80%, 79%, and 78%.

Third Embodiment

Figure 13:
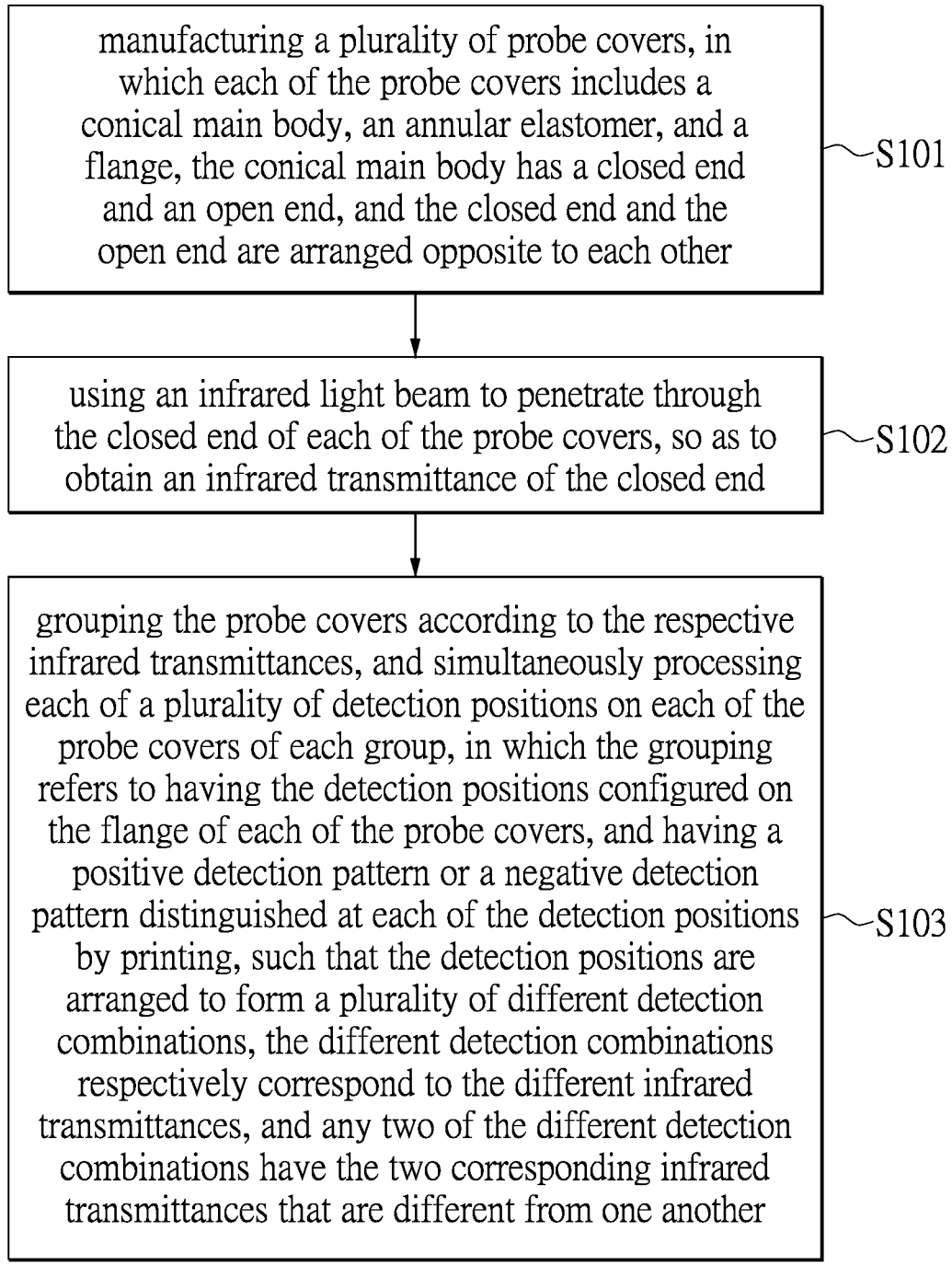
FIG. 13 is a schematic diagram illustrating steps of a grouping method of the probe cover for the ear thermometer according to the present disclosure.

Reference is made to FIG. 13. A grouping method of the probe cover U for the ear thermometer T is provided by the present disclosure, and the grouping method is capable of grouping the mass-produced probe covers U according to their respective infrared transmittances. It should be noted that the grouping method of the probe cover U for the ear thermometer T provided by the present disclosure is implemented through the probe covers U for the ear thermometer T of the first and the second embodiments. Therefore, reference can be made to the first embodiment, the second embodiment, and FIG. 1 to FIG. 12 with regard to the descriptions of the probe cover U for the ear thermometer T in the present embodiment. The structural features of the probe cover U for the ear thermometer T as referred to in the present embodiment will not be reiterated herein. However, the implementation of the grouping method of the probe cover U for the ear thermometer T provided by the present disclosure is not limited to the probe cover U for the ear thermometer T provided by the present disclosure.

The grouping method of the probe cover U for the ear thermometer T at least includes steps as follows.

Step S101: Manufacturing a plurality of the probe covers U. Each of the probe covers U includes the conical main body 1, the annular elastomer 2, and the flange 3. The conical main body 1 has the closed end 11 and the open end 12, the closed end 11 and the open end 12 are arranged opposite to each other, and the flange 3 includes at least one recessed portion 31.

Step S102: Using an infrared light beam to penetrate through the closed end 11 of each of the probe covers U, so as to obtain an infrared transmittance of the closed end 11.

Step S103: Grouping the probe covers U according to the infrared transmittance of each of the probe covers U, and simultaneously processing each of the detection positions 30 on each of the probe covers U of each group. The grouping refers to having the detection positions 30 configured on the flange 3 of each of the probe covers U, and having the positive detection pattern 3a or the negative detection pattern 3b distinguished at each of the detection positions 30 by printing, such that the detection positions 30 are arranged to form the different detection combinations. The different detection combinations respectively correspond to the different infrared transmittances, and any two of the different detection combinations have the two corresponding infrared transmittances that are different from one another.

Specifically, the processing of each of the detection positions 30 on each of the probe covers U of each group indicates that each of the detection positions 30 is processed to be either the positive detection pattern 3a or the negative detection pattern 3b according to the detection combination to be formed for each group during the grouping. When the detection position 30 is the positive detection pattern 3a, the flange 3 is processed to have an opening formed at the detection position 30. When the detection position 30 is the negative detection pattern 3b, the flange 3 has no opening formed at the detection position 30.

Further to the above, the positive detection pattern 3a and the negative detection pattern 3b can also be in other forms. For example, the positive detection pattern 3a can refer to the flange 3 being formed by a light-permeable material at the detection position 30, and the negative detection pattern 3b can refer to the flange 3 being formed by an opaque material at the detection position 30 (not shown in the drawings). The activation elements T3 of the ear thermometer T that correspond to the detection positions 30 on the flange 3 of the probe cover U can be optoelectronic switches (optoelectronic sensors). Translucence or opaqueness of the detection positions 30 on the flange 3 of the probe cover U can be used to block a light beam emitted from the optoelectronic switches or allow the same to penetrate through. In this way, the infrared transmittance of the probe cover U can be detected.

Beneficial Effects of the Embodiments

One of the beneficial effects of the present disclosure is that, in the probe cover U for the ear thermometer T and the grouping method of the same provided by the present disclosure, through the technical solutions of "the flange 3 of the probe cover U having the plurality of detection positions 30, and each of the detection positions 30 having the positive detection pattern 3a or the negative detection pattern 3b, such that the detection positions 30 are arranged to form the plurality of different detection combinations" and "the different detection combinations respectively corresponding to the different infrared transmittances, and any two of the different detection combinations having the two corresponding infrared transmittances that are different from one another", the ear thermometer T that has the probe cover U placed thereon can quickly determine the infrared transmittance of the probe cover U, and then calculate and make adjustments according to a value of the infrared transmittance, thereby accurately measuring a temperature of a human body.

Specifically, since the probe cover U for the ear thermometer T provided by the present disclosure is placed on the probe T2 of the ear thermometer T, there are the plurality of activation elements T3 on the ear thermometer T that correspond to the plurality of detection positions 30 on the flange 3 of the probe cover U. When the probe cover U is placed on the probe T2 of the ear thermometer T, the activation elements T3 are in contact with the detection positions 30 on the flange 3 of the probe cover U, thereby detecting the infrared transmittance of the probe cover U. That is to say, through the detection positions 30 on the flange 3 of the probe cover U being arranged to form the plurality of different detection combinations, the activation elements T3 are able to detect an infrared transmittance for each different probe cover U.

More specifically, for the probe cover U of the present disclosure, through the engagement of the recessed portion 31 with the protrusion T1 of the ear thermometer T, the detection positions 30 on the flange 3 of the probe cover U can correspond to the activation elements T3 on the ear thermometer T. When the probe cover U is placed on the probe T2 of the ear thermometer T, the design of the recessed portion 31 of the probe cover U can prevent the detection positions 30 from being misaligned with the activation elements T3 due to a rotation of the probe cover U.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A probe cover for an ear thermometer, comprising:
a conical main body having a closed end and an open end, wherein the closed end and the open end are arranged opposite to each other, the closed end is penetrable by infrared rays, and the closed end has different infrared transmittances according to thickness variations of the closed end;
an annular elastomer connected to the open end of the conical main body; and
a flange connected to the annular elastomer, the annular elastomer being located between the conical main body and the flange;
wherein the flange has a plurality of detection positions;
wherein each of the detection positions has a positive detection pattern or a negative detection pattern, such that the detection positions are arranged to form a plurality of different detection combinations; and
wherein the different detection combinations respectively correspond to the different infrared transmittances, and any two of the different detection combinations have the two corresponding infrared transmittances that are different from one another.

2. The probe cover according to claim 1, wherein the positive detection pattern refers to the flange having an opening formed at the detection positon, and the negative detection pattern refers to the flange having no opening formed at the detection position.

3. The probe cover according to claim 1, wherein the positive detection pattern refers to the flange being formed by a light-permeable material at the detection position, and the negative detection pattern refers to the flange being formed by an opaque material at the detection position.

4. The probe cover according to claim 1, wherein the annular elastomer includes a first abutting portion and a second abutting portion opposite to the first abutting portion; and wherein the first abutting portion and the second abutting portion are fastened in a groove of a probe of the ear thermometer, and the groove surrounds an outer surface of the probe.

5. The probe cover according to claim 1, wherein, when a quantity of the detection positions is set to be two, a quantity of the detection combinations is set to be at most four.

6. The probe cover according to claim 1, wherein, when a quantity of the detection positions is set to be three, a quantity of the detection combinations is set to be at most eight.

7. The probe cover according to claim 1, further comprising at least one recessed portion formed on the flange.

8. The probe cover according to claim 7, wherein the conical main body has a central axis, and the central axis passes through a center of the closed end and a center of the open end; wherein the at least one recessed portion is recessed in a direction toward the central axis; and wherein the at least one recessed portion is used to engage with at least one protrusion of the ear thermometer, and the at least one protrusion is disposed near a probe of the ear thermometer and protrudes in a direction parallel to the central axis.

* * * * *